(12) United States Patent
Malik et al.

(10) Patent No.: US 6,867,311 B2
(45) Date of Patent: Mar. 15, 2005

(54) CLEAN, HIGH-YIELD PREPARATION OF S,S AND R,S AMINO ACID ISOSTERES

(75) Inventors: Aslam A. Malik, Cameron Park, CA (US); Todd E. Clement, Folsom, CA (US); Hasan Palandoken, Woodland, CA (US); James Robinson, III, Sacramento, CA (US); Joy A. Stringer, Carmichael, CA (US)

(73) Assignee: Aerojet Fine Chemicals LLC, Sacramento, CA (US)

( * ) Notice: Subject to any disclaimer, the term of this patent is extended or adjusted under 35 U.S.C. 154(b) by 0 days.

(21) Appl. No.: 10/414,541

(22) Filed: Apr. 14, 2003

(65) Prior Publication Data

US 2003/0225292 A1 Dec. 4, 2003

Related U.S. Application Data

(62) Division of application No. 09/321,645, filed on May 28, 1999, now Pat. No. 6,605,732.
(60) Provisional application No. 60/132,278, filed on May 3, 1999.

(51) Int. Cl.$^7$ ............................................. C07D 301/24
(52) U.S. Cl. ....................................................... 549/519
(58) Field of Search ......................................... 549/519

(56) References Cited

U.S. PATENT DOCUMENTS 5,684,176 A  11/1997  Hilpert
5,817,778 A  10/1998  Archibald et al.
5,847,144 A  12/1998  Hilpert
5,854,405 A  12/1998  Archibald et al.

OTHER PUBLICATIONS

Barluenga et al., *J. Org. Chem.*, 62:4974–5977 (1997).
Barrish et al., *J. Med. Chem.*, 37(12):1758–1768 (1994).
Beaulieu et al., *J. Org. Chem.*, 62:3440–3448 (1997).
Chen et al., *J. Med. Chem.*, 39:1991–2007 (1996).
Dufour et al., *J. Chem. Soc. Perkin Trans. I*, 1895–1899 (1986).
Ghosh et al., *J. Org. Chem.*, 62:6080–6082 (1997).
Liu et al., *Org. Proc. Res. Dev.*, 1:45–54 (1997).
Luly et al., *J. Org. Chem.*, 52:1487–1492 (1987).
Parkes et al., *J. Org. Chem.*, 59:3656–3684 (1994).
Raddatz et al., *J. Med. Chem.*, 34(11)3267–3280 (1991).
Shaw, *Methods in Enzymology*, 11:677–688 (1967).
Shibata et al., *Chem. Pharm. Bull.*, 46(4):733–735 (1998).

*Primary Examiner*—Taofiq Solola
(74) *Attorney, Agent, or Firm*—Townsend & Townsend & Crew LLP

(57) ABSTRACT

The present invention provides compounds and methods that can be used to convert the intermediate halomethyl ketones (HMKs), e.g., chloromethyl ketones, to the corresponding S,S- and R,S-diastereomers. More particularly, the present invention provides: (1) reduction methods; (2) inversion methods; and (3) methods involving the epoxidation of alkenes. Using the various methods of the present invention, the R,S-epoxide and the intermediary compounds can be prepared reliably, in high yields and in high purity.

14 Claims, 4 Drawing Sheets

CLEAN, HIGH-YIELD PREPARATION OF S,S AND R,S AMINO ACID ISOSTERES

CROSS-REFERENCE TO RELATED APPLICATIONS

Divisional filed on May 28, 1999, now U.S. Pat. No. 6,605,732, which claims the benefit of U.S. Provisional Patent Application Ser. No. 60/132,278, filed May 3, 1999, which is incorporated herein by reference in its entirety for all purposes.

BACKGROUND OF THE INVENTION

Human immunodeficiency virus (HIV), the causative agent of acquired immunodeficiency syndrome (AIDS), encodes three enzymes, including the well-characterized proteinase belonging to the aspartic proteinase family, the HIV protease. Inhibition of this enzyme has been regarded as a promising approach for treating AIDS. Hydroxyethylamine isosteres have been extensively utilized in the synthesis of potent and selective HIV protease inhibitors. However, this modern generation of HIV protease inhibitors has created an interesting challenge for the synthetic organic chemist. Advanced x-ray structural analysis has allowed for the design of molecules that fit closely into active sites on enzymes creating very effective drug molecules. Unfortunately, these molecules, designed by molecular shape, are often difficult to produce using conventional chemistry.

The modern generation of HIV inhibitors has structural similarities in a central three-carbon piece containing two chiral carbons that link two larger groups on each side (see, e.g., Parkes, et al., *J. Org. Chem.* 1994 39, 3656). Numerous synthetic routes to these isosteres have been developed. As illustrated below, a common strategy to prepare the linking group starts with an amino acid, such as phenylalanine, to set the chirality of the first carbon. Then, the linking group is completed by a series of reactions including a one-carbon homologization during which the old amino acid carbon is transformed into a hydroxy-functionalized carbon having the correct chirality. However, the commercial production of isosteres by this method presents serious challenges, generally requiring low-temperature organometallic reactions (Baragua, et al., J. Org. Chem. 1997, 62, 6080) or the use of exotic reagents.

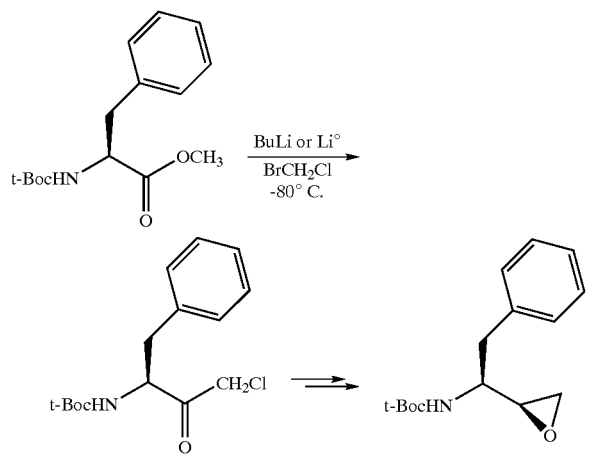

A second approach, which is illustrated below, is to convert the amino acid to an aldehyde and to add the carbon by use of a Wittig reaction to give an olefin (see, Luly, et al., *J. Org. Chem.* 1987, 52, 1487). The olefin is then epoxidized. Alternatively, the aldehyde can be reacted with nitromethane, cyanide (see, Shibata, et al., *Chem. Pharm. Bull.* 1998, 46, 733) or carbene sources (see, Liu, et al., Org. Proc. Res. Dev. 1997, 1, 45). Instability and difficulty in preparation of the aldehyde make these routes undesirable (see, Beaulieu, et al., *J. Org. Chem.* 1997, 62, 3440).

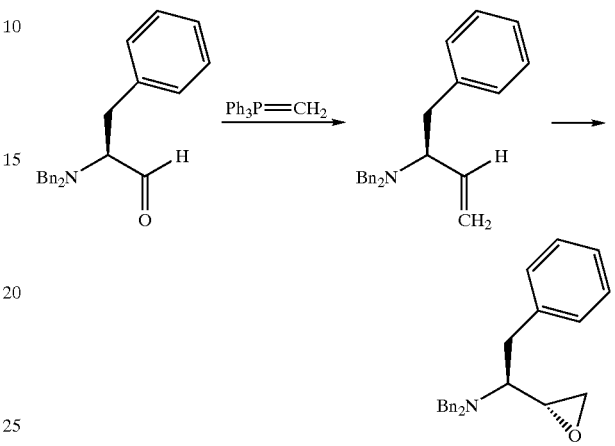

Other routes that have been published, but not commercialized are illustrated in FIG. 1.

One of the best reagents that can be used to add a single carbon to amino acids is diazomethane because it gives high yields and few side-products. In addition, diazomethane reactions are very clean, generating only nitrogen as a by-product. HIV inhibitor molecules need high purity because of the high daily doses required. As such, diazomethane is an ideal reagent for making high purity compounds. In spite of the documented hazards of diazomethane, processes have recently been developed that permit the commercial scale use of diazomethane to convert amino acids to the homologous chloromethyl ketones (see, U.S. Pat. No. 5,817,778, which issued to Archibald, et al. on Oct. 6, 1998; and U.S. Pat. No. 5,854,405, which issued to Archibald, et al. on Dec. 29, 1998). FIG. 2 illustrates examples of HIV protease inhibitors wherein the central linking group can be synthesized by the commercial use of diazomethane. FIG. 3 illustrates a general reaction scheme that can be used to prepare the S,S-epoxide compound using diazomethane.

The most useful amino acid isosteres are based on phenylanaline. The key intermediate in the synthesis of Sequinivir® (Roche) and Aprenavir® (Glaxo Wellcome) is the (S,S-)N-t-butoxycarbonyl-1,2-epoxy-4-phenyl-3-butanamine. Several other protease inhibitors, such as those described in Chem, et al. (*J. Med. Chem.* 1996, 39, 1991) or those under development (e.g., BMS-234475 or BMS-232623), use the diastereomeric (R,S-)N-t-butoxycarbonyl-1,2-epoxy-4-phenyl-3-butanamine.

Beginning with readily available (L)-phenylanaline, one is able to manufacture N-t-butoxycarbonyl-1-chloro-2-keto-4-phenylbutanamine (called "chloroketone" or "CMK") using the methods described in the literature (see, e.g., Parkes, et al., *J. Org. Chem.* 1994 39, 3656; Shaw, E., *Methods in Enzymology* (Academic Press, New York, London), 1967, 11, 677; and Dufour, et al., *J. Chem. Soc. Perkin Trans. I* 1986, 1895, the teachings of which are incorporated herein by reference). However, what are needed in the art are methods that allow one to produce reliably and in high-yields either diastereomer, i.e., the S,S or the R,S, from the common chloroketone starting material (see, FIG. 4). Quite surprisingly, the present invention fulfills this and other needs.

SUMMARY OF THE INVENTION

The present invention provides compounds and methods that can be used to convert the intermediate halomethyl ketones (HMKs), e.g., chloromethyl ketones, to the corresponding S,S- and R,S-diastereomers. It is these chiral centers that determine the chiral centers in the HIV protease inhibitor and, thus, the efficacy of the drug. As explained herein, the present invention provides (1) reduction methods; (2) inversion methods; and (3) methods for preparing alkenes that, in turn, can undergo epoxidation reactions to form the desired R,S-epoxide. Using the various methods of the present invention, the R,S-epoxide and the intermediary compounds can be prepared reliably, in high yields and in high purity.

As such, in one embodiment, the present invention provides a method for selectively preparing an R,S-halomethyl alcohol (R,S-HMA) compound having the following general formula:

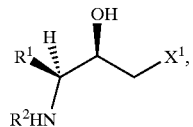

the method comprising: reducing a compound having the following general formula:

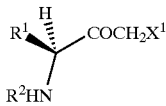

with a non-chelating, bulky reducing agent to form the R,S-HMA compound. In the above formulae, $R^1$ is an amino acid side chain (e.g., a benzyl group, an S-phenyl group, an alkyl group and a para-nitrobenzene group, etc.); $R^2$ is a blocking or protecting group (e.g., Boc, Cbz, Moc, etc.); and $X^1$ is a leaving group (e.g., a halo group, such as chloro). In a presently preferred embodiment, the non-chelating, bulky reducing agent is a member selected from the group consisting of LATBH and STBH. In another presently preferred embodiment, the reduction is carried out in a solvent such as diethyl ether. Once formed, the R,S-HMA can be reacted with an alkali metal base to form an R,S-epoxide.

In another embodiment, the present invention provides a method for preparing an R,S-halomethyl alcohol (R,S-HMA) compound having the following general formula:

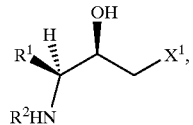

the method comprising: reducing a halomethyl ketone (HMK) compound having the following general formula:

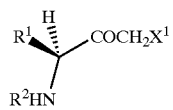

with a reducing agent selected from the group consisting of sodium cyanoborohydride, cerium chloride/sodium borohydride, K-Selectride®, KS-Selectride® and (+)-Dip Chloride™ to form the R,S-HMA compound. In this method, $R^1$ is an amino acid side chain; $R^2$ is a blocking group; and $X^1$ is a leaving group. Again, once formed, the R,S-HMA can be reacted with an alkali metal base to form an R,S-epoxide.

In another aspect, the present invention provides inversion methods that can be used to selectively prepare the R,S-epoxide. In one embodiment of the inversion method, R,S-epoxide is prepared by a four step process. More particularly, in one embodiment of the inversion method, the present invention provides a method for preparing an R,S-epoxide having the following general formula:

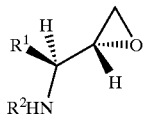

the method comprising: (a) reducing a halomethyl ketone (HMK) compound having the following general formula:

(I)

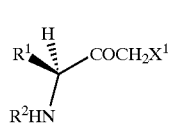

with a reducing agent to form an S,S-halomethyl alcohol (S,S-HMA) compound having the following general formula:

(II)

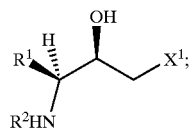

(b) contacting the S,S-HMA compound of Formula II with a member selected from the group consisting of arylsulfonyl halides and alkylsulfonyl halides in the presence of an amine to form an S,S-halomethyl sulfonyl (S,S-HMS) compound having the following general formula:

(III)

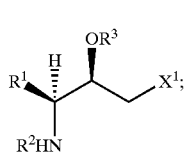

(c) contacting the S,S-HMS compound of Formula III with an acetate in the presence of a phase transfer catalyst and water to form an R,S-halomethyl acetate (R,S-HMAc) compound having the following general formula:

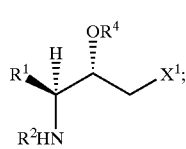

(IV)

and (d) contacting the R,S-HMAc compound of Formula IV with an alkali metal base to form the R,S-epoxide. In the above formulae, R¹ is an amino acid side chain (e.g., a benzyl group, an S-phenyl group, an alkyl group, a para-nitrobenzene group, etc.); R² is a blocking or protecting group; X¹ is a leaving group (i.e., a halo group, such as chloro); R³ is a functional group including, but not limited to, arylsulfonyls and alkylsulfonyls (e.g., a mesyl group, a tosyl group, a triflate group, a nosyl group, etc.); and R⁴ is an acyl group derived from the acetate (e.g., an acetyl group).

In another embodiment of the inversion method, the present invention provides a method for preparing an R,S-epoxide compound having the following general formula:

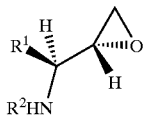

the method comprising: (a) contacting an S,S-halomethyl sulfonyl (S,S-HMS) compound having the following general formula:

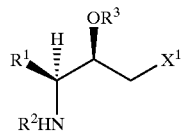

with a carbamate-forming acetate to form a cyclic carbamate; and (b) contacting the cyclic carbamate with an alkali metal base to form the R,S-epoxide. In the above formulae, R¹, R², R³ and X¹ are as defined above. In a presently preferred embodiment, the carbamate-forming acetate is sodium trichloroacetate.

In yet another aspect, the present invention provides a method for preparing R,S-epoxide by the epoxidation of an alkene. More particularly, the present invention provides a method for preparing an alkene having the following general formula:

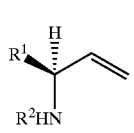

(IV)' the method comprising: (a) contacting a compound having the following general formula:

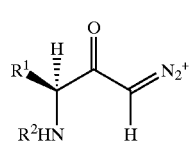

(I)

with a hydrohalo acid to form a compound having the following general formula:

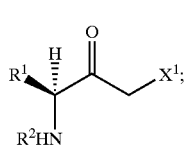

(II)

(b) reducing a compound of Formula II with a reducing agent to form a compound having the following general formula:

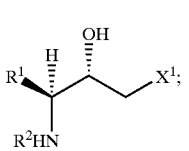

(III)

and (c) dehalohydroxylating a compound of Formula III to form the alkene. In the above formulae, R¹, R², and X¹ are as defined above. Once prepared, the alkene can be converted to the R,S-epoxide using, for example, m-chloroperbenzoic acid.

Other features, objects and advantages of the invention and its preferred embodiments will become apparent from the detailed description which follows.

BRIEF DESCRIPTION OF THE DRAWINGS

FIG. 1(A) illustrates a method described by Ng, et al., Org. Proc. Res. Dev. 1997, 1, 46; and Beaulieu, et al., J. Org. Chem. 1997, 62, 3441. FIG. 1(B) illustrates a method described by Parkes, et al. J. Org. Chem. 1994, 59, 3656.

DETAILED DESCRIPTION OF THE INVENTION AND PREFERRED EMBODIMENTS

Figure 1:
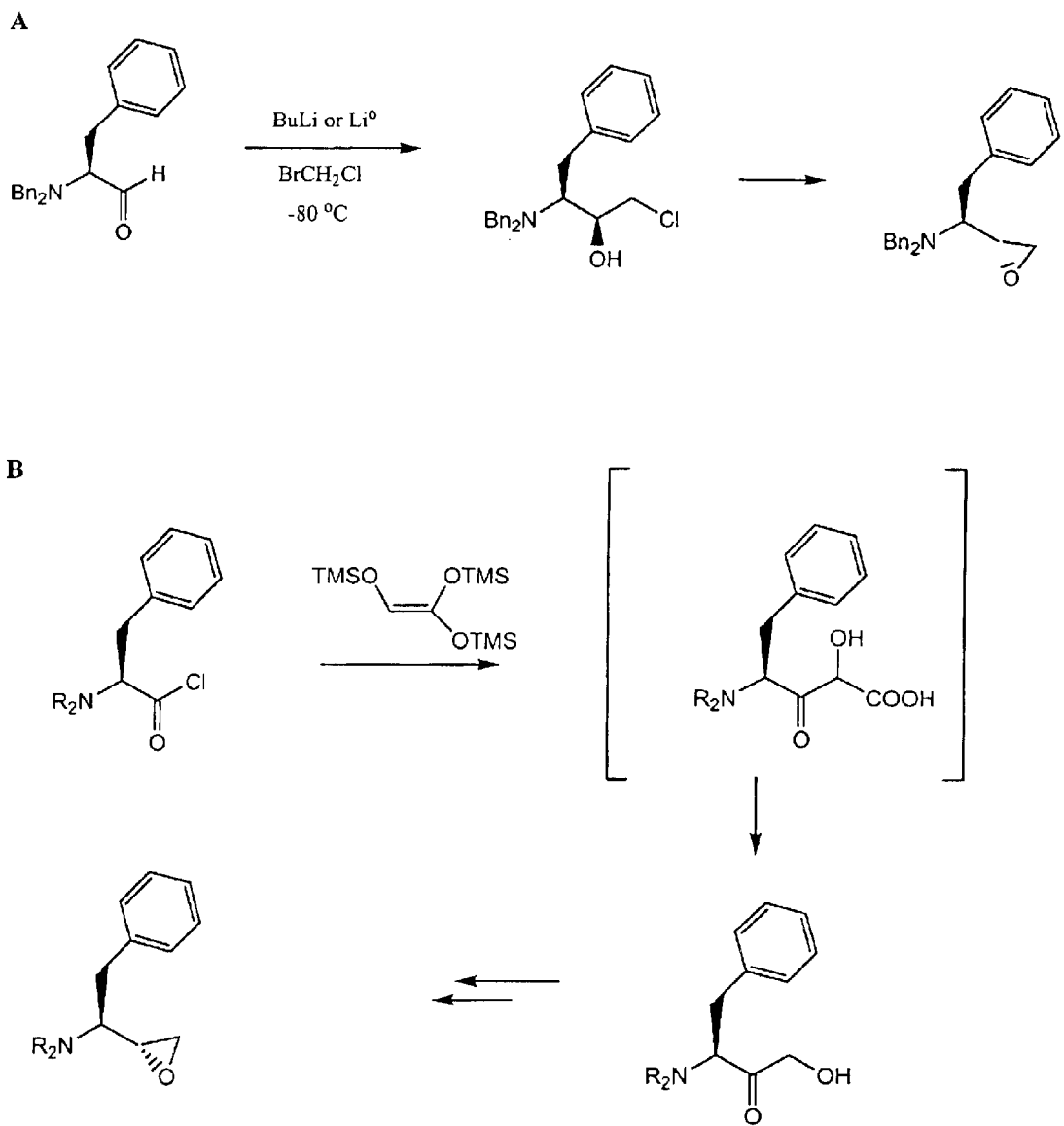
FIG. 1 illustrates various routes that can be used to prepare an R,S-epoxide.
Figure 2:
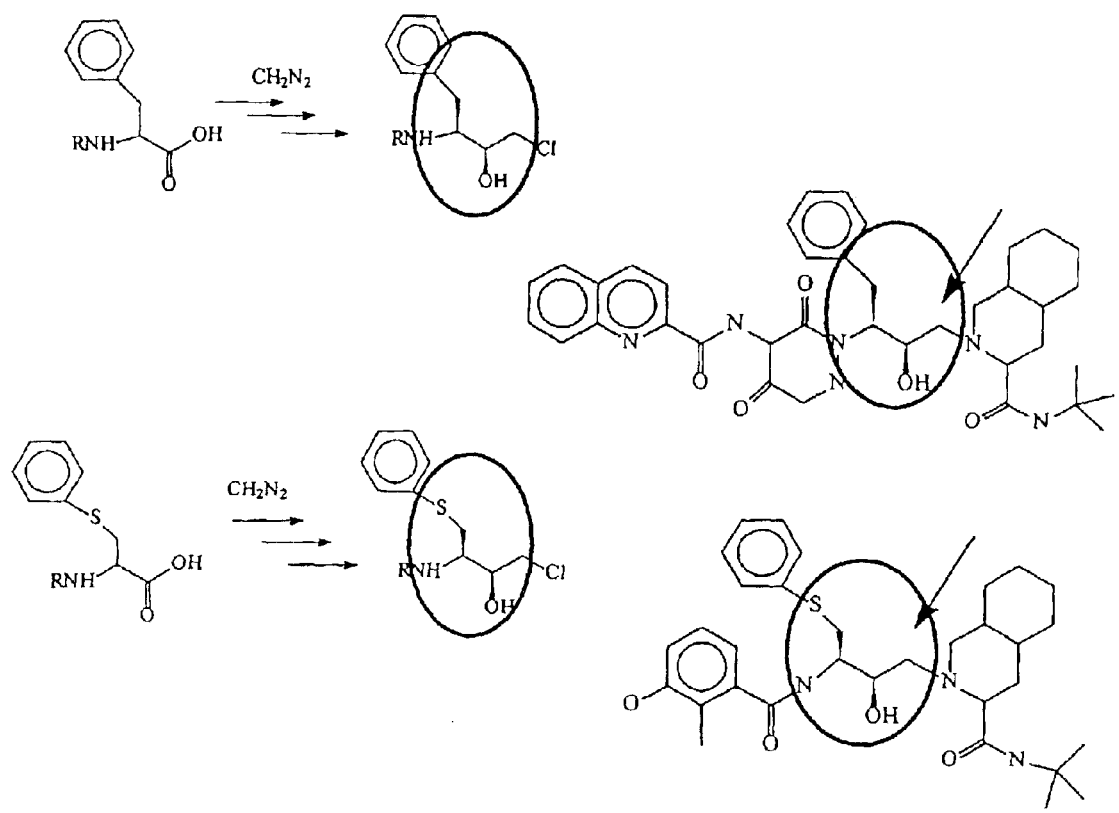
FIG. 2 illustrates examples of HMV protease inhibitors where the central linking group can be synthesized by commercial use of diazomethane.
Figure 3:
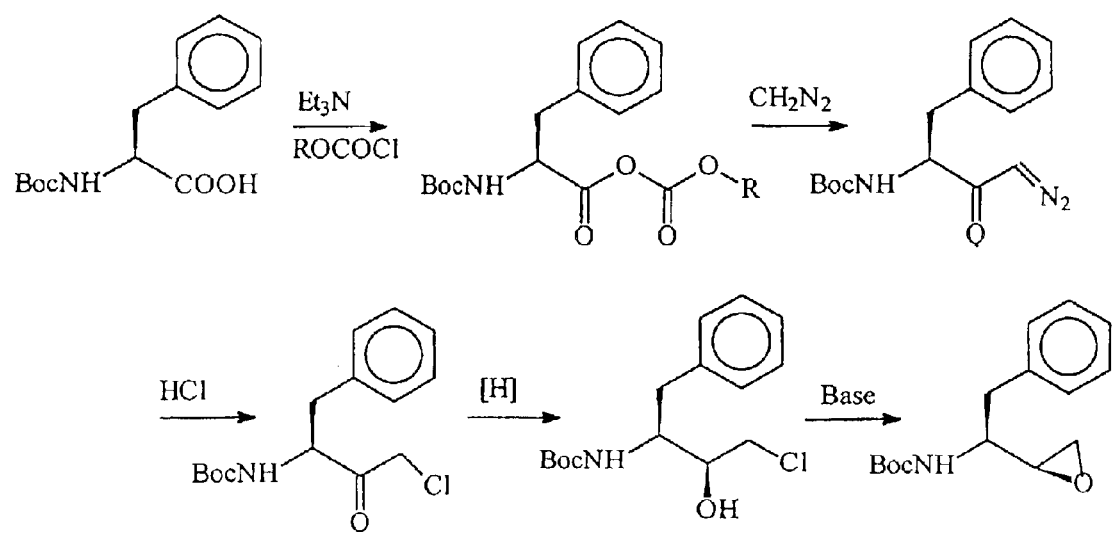
FIG. 3 illustrates a general reaction scheme that can be used to prepare the epoxide compound.
Figure 4:
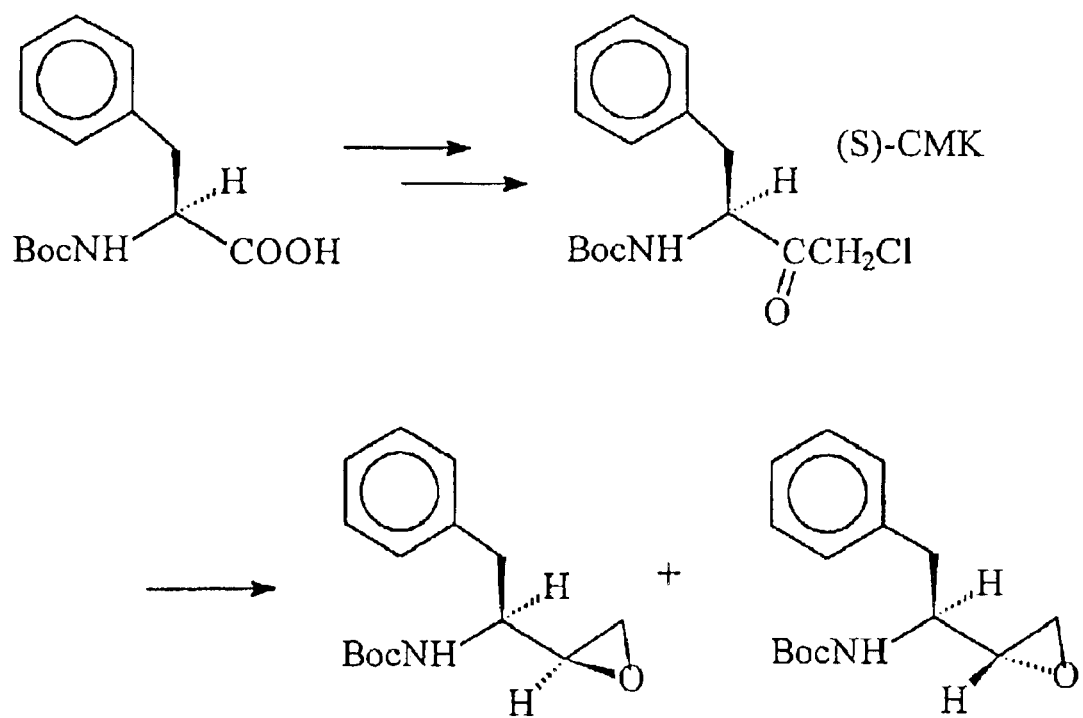
FIG. 4 illustrates the two diastereomers that can be formed from the common chloroketone starting material, i.e., S,S-epoxide and R,S-epoxide.

The present invention provides various compounds and methods that can be used to prepare both reliable and in high yields either diastereomer, i.e., the S,S- or the R,S-, from the common halomethyl ketone (e.g., chloromethyl ketone) starting material. More particularly, as explained herein in greater detail, the present invention provides (1) reduction methods; (2) inversion methods, and (3) methods involving the epoxidation of alkenes.

A. The Reduction Methods

A variety of reducing agents can be used to reduce a halomethyl ketone (HMK) to a halomethyl alcohol (HMA) (see, Table I). However, under most conditions, the predominate diastereomer is the 2S,3S-HMA. For instance, reduction of HMK with sodium borohydride in ethanol (Chen, et al., *J. Med. Chem.* 1996, 39, 1991) produces a 1:4 mixture of R,S:S,S HMA in near quantitative yield. Moreover, the reduction of HMK with aluminium isopropoxide in isopropanol can give ratios as high as 1:18 in favor of the S,S-isomer (see, U.S. Pat. Nos. 5,684,176 and 5,847,144, both of which issued to Hilpert). Thus, commercial routes to S,S-HMA are easily achieved.

In contrast, the preparation of the R,S-isomer is much more difficult. A slight increase in the R,S-HMA:S,S-HMA ratio is achieved when the reaction solvent, ethanol, is replaced with THF. Further enhancement in the R,S-HMA:S,S-HMA ratio is obtained when the reduction is carried out in the presence of $CeCl_3$ (Barluenga, *J. Org. Chem.* 1997, 62,5974); but even then the ratio of R,S-HMA:S,S-HMA is <1:1. Other reducing agents, such as $LiAlH_4$, sodium cyanoborohydride, potassium borohydride, etc., under a variety of reaction conditions, also fail to provide >1:1 R,S-HMA:S,S-HMA. In fact, a perusal of the literature supports the observation that S,S-HMA is the preferred isomer using coordinating reducing reagents, such as borohydrides or aluminium hydrides (see, U.S. Pat. Nos. 5,684,176 and 5,847,144, both of which issued to Hilpert).

In contrast to the teachings of both the scientific and patent literature, it has now been discovered that the reduction of HMK proceeds with high R,S diastereoselectivity when lithium aluminum t-butoxyhydride (LATBH) is used as the reducing agent. Quite surprisingly and in contrast to the findings of the prior art, it has been found that the reduction of HMK with LATBH in, for example, diethyl-ether provides a 8:1 mixture of R,S-HMA:S,S-HMA in 97% yield. This high diastereofacial selectivity of the LATBH reducing agent is unusual since reduction of HMK with similar reducing agents, such as lithium aluminum hydride or sodium borohydride, do not favor R,S diastereoselectivity (see, U.S. Pat. Nos. 5,684,176 and 5,847,144, both of which issued to Hilpert).

TABLE I

HMK Reductions:

| Reagent(s) | Solvent(s) | Temp | Time | R,S:S,S |
|---|---|---|---|---|
| Li(OtBu)3AlH | Et2O | 0 C. | 3 Hrs | 8:1 |
| (+)-Dip Chloride ™ (1.4eq) | THF | 5C-RT | 12 Hrs | 5:1 |
| K-Selectride ® | THF | Reflux | 2 Hrs | 2:1 |
| K-Selectride ®/Ti(OiPr)4 | THF | 25 C. | 30 Min | 2:1 |
| KS-Selectride ® | THF | RT | 2 Hrs | 2:1 |
| K-Select./MgBr2*OEt2 | THF | RT | 30 Min | 2.6:1 |
| R-Alpine Borane(Conc.) | THF | Reflux | 9 Dys | 1:1 |
| L-Selectride ® | THF | R.T. | 1 Hr | 0.9:1 |
| NaBH4/CeCl3(anh.) | THF | RT | 2 Hrs | 0.8:1 |
| N-Selectride ® | EtOH/THF | R.T. | 2 Hrs | 0.7:1 |
| NaBH4/CeCl3*7H2O | THF | 25 C. | 18 Hrs | 0.7:1 |
| NaBH4/EDTA(Na2*2H2O) | THF | RT | 30 Min | 0.7:1 |
| NaCNBH3 | THF | RT | 36 Hrs | 0.7:1 |
| (+)-2-Butanol/NaBH4 | THF | RT | 1 Hr | 0.6:1 |
| Cp2TiBH4 | Glyme | R.T. | 30 Min | 0.6:1 |
| NaBH4 | THF | 25 C. | 2 Hrs | 0.6:1 |
| NaBH4/(−)-2-Butanol | THF | RT | 30 Min | 0.6:1 |
| NaBH4/Al(OiPr)4 | THF | Reflux | 2 Hrs | 0.6:1 |
| NaBH4/DiacetoneDglucose | THF | RT | 12 Hrs | 0.6:1 |
| NaBH4/EDTA | THF | RT | 12 Hrs | 0.6:1 |
| NaBH4/L-Tartaric Acid | THF | 5 C. | 1 Hr | 0.6:1 |
| NaBH4/MgBr2*OEt2 | THF | RT | 1 Hr | 0.6:1 |

TABLE I-continued

HMK Reductions:

| Reagent(s) | Solvent(s) | Temp | Time | R,S:S,S |
|---|---|---|---|---|
| BH3-t-butylamine | THF | R.T. | 1 Hr | 0.5:1 |
| LAH | THF | 25 C. | 1 Hr | 0.5:1 |
| LS-Selectride ® | THF | RT | 1 Hr | 0.5:1 |
| NaBH4/D-Tartaric Acid | THF | RT | 30 Min | 0.5:1 |
| (+)-2-Butanol * BH3 | THF | RT | 1 Hr | 0.4:1 |
| NaBH4/CaCl2 | MeOH | R.T. | 1 Hr | 0.4:1 |
| AminoAlcohol Borane | THF | 25 C. | 12 Hrs | 0.3:1 |
| Na(PEG)2BH2 | THF | RT | 30 Min | 0.3:1 |
| THF*BH3 | EtOH/THF | R.T. | 2 Hrs | 0.2:1 |
| Al(iOPr)3 | IPA | 50 C. | 3 Dys | 0.05:1 |
| Na HB(OCH3)3 | MeOH | RT | 1 Hr | 1:1 |

As such, in one embodiment, the present invention provides a method for preparing an R,S-halomethyl alcohol (R,S-HMA) compound having the following general formula:

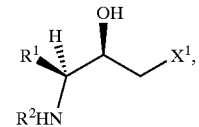

the method comprising: reducing a compound having the following general formula:

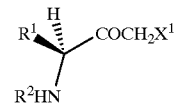

with a non-chelating, bulky reducing agent to form the R,S-HMA compound.

In the above formulae, $R^1$ is an amino acid side chain. More particularly, in the above formulae, $R^1$ is a side chain from any of the naturally occurring amino acids or amino acid mimetics. In a preferred embodiment, $R^1$ is a benzyl group, a substituted benzyl group, an S-phenyl group, an alkyl group or a para-nitrobenzene group. In an even more preferred embodiment, $R^1$ is a benzyl group. $R^2$, in the above formulae, is a blocking or protecting group. It will be readily apparent to those of skill in the art that suitable-amino blocking groups include, for example, those known to be useful in the art of stepwise synthesis of peptides. Included are acyl type protecting groups (e.g., formyl, trifluoroacetyl, acetyl, etc.), aromatic urethane type protecting groups (e.g., benzyloxycarboyl (Cbz), substituted Cbz, etc.), aliphatic urethane type protecting groups (e.g., t-butyloxycarbonyl (Boc), isopropylcarbonyl, cyclohexyloxycarbonyl, etc.) and alkyl type protecting groups (e.g., benzyl, triphenylmethyl, etc.). In a presently preferred embodiment, the blocking group is selected from the group consisting of Boc, Cbz and Moc. In the above formulae, $X^1$ is a leaving group. Suitable leaving groups will be readily apparent to those of skill in the art. In a presently preferred embodiment, the leaving group is a halo group (e.g., Cl, Br, F or I). In an even more preferred embodiment, $X^1$ is a chloro or bromo group. Although many of the compounds disclosed herein contain the exemplar designation "halo," such as halomethyl ketone (HMK) or halomethyl alcohol (HMA), it will be readily apparent to those of skill in the art that other leaving groups can be used in place of the halo group.

In the above embodiment, the reduction is carried out using a non-chelating, bulky reducing agent. It has surprisingly been discovered that non-chelating, bulky reducing agents favor the S,R-diastereomer. Examples of non-chelating, bulky reducing agents suitable for use in the methods of the present invention include, but are not limited to, lithium aluminum t-butoxyhydride (LATBH), sodium tris-t-butoxyborohydride (STBH). In a presently preferred embodiment, the non-chelating, bulky reducing agent is LATBH. Once formed, the R,S-HMA can be reacted with an alkali metal base to form an R,S-epoxide. An exemplar embodiment of the above method is illustrated by the following reaction scheme:

Synthesis of R,S-Boc-Epoxide by LATBH Reduction

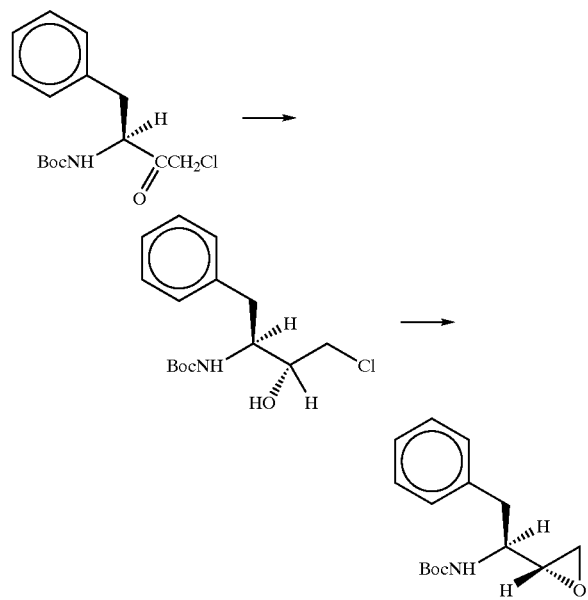

In this embodiment, the reduction is preferably carried out in a solvent. It will be readily apparent to those of skill in the art that numerous solvents can be used. Exemplar solvents include, but are not limited to, the following: diethyl ether, THF, MTBE and mixtures thereof. Quite surprisingly, it has been found that the reduction of LATBH is dependent on the solvent employed. For instance, when diethyl ether is used as the solvent, a 8:1 mixture of R,S-HMA:S,S-HMA is obtained. However, when THF or MTBE is used as the solvent the ratio of R,S-HMA:S,S-HMA is less than or equal to about 2:1. Based on these result, it is thought that a variety of factors, such as steric, solvation and chelation, are responsible for the high R,S diastereoselectivity observed in LATBH reduction of HMK. Thus, when LATBH is used as the reducing agent, diethyl ether is preferably used as the solvent.

LATBH is commercially available as a white powder and is used as a suspension in diethyl ether. Alternately, LATBH can be prepared in situ by the reaction of LAH with 3 equivalents of t-butylalcohol in diethylether and then reacted with HMK. The best solvent, as judged on basis of R,S-diastereoselectivity, is diethyl ether. However, the solubility of HMK in diethyl ether is relatively low and a large amount of diethyl ether is needed to dissolve CMK, thereby reducing reactor efficiency to some extent. The reactor efficiency can be improved by either adding HMK as a solid or, alternatively, as a solution in a secondary solvent (e.g., THF, toluene, ethyl acetate, etc.) to a suspension of LATBH in diethyl ether. The reaction rate is not affected, but the diastereoselectivity can be reduced from 8:1 in pure diethyl ether to about 5:1 with the above modifications.

In this embodiment, the reduction can be carried out at a temperature ranging from about −30° C. to about 25° C. In a presently preferred embodiment, the reduction is carried out at a temperature ranging from about −5° C. to about 5° C. At lower temperatures, larger amounts of solvent are needed to maintain homogeneity; whereas at high temperatures, formation of the epoxide, resulting from intramolecular cyclization, is observed. At 0° C., the reduction reaction is rapid and is complete in less than about 30 minutes. It will be readily apparent to those of skill in the art that the progress of the reduction reaction can be monitored by, for example, HPLC, and the reaction is deemed complete when the amount of unreacted HMK is less than about 1%.

In another embodiment, the present invention provides a method for preparing an R,S-halomethyl alcohol (R,S-HMA) compound having the following general formula:

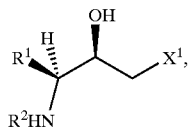

the method comprising: reducing a halomethyl ketone (HMK) compound having the following general formula:

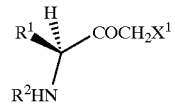

with a reducing agent selected from the group consisting of sodium cyanoborohydride, cerium chloride/sodium borohydride, K-Selectride®, KS-Selectride® and (+)-Dip Chloride™ to form the R,S-HMA compound. In this method, $R^1$ is an amino acid side chain; $R^2$ is a blocking group; and $X^1$ is a leaving group. It will be readily apparent to those of skill in the art that the foregoing discussions relating to $R^1$, $R^2$ and $X^1$ and their preferred embodiments are fully applicable to this method and, thus, will not be repeated.

As with the previously described method, the reduction is preferably carried out in a solvent. It will be readily apparent to those of skill in the art that numerous solvents can be used. Exemplar solvents include, but are not limited to, the following: diethyl ether, THF, MTBE and mixtures thereof. In a preferred embodiment, diethyl ether or THF is employed as the solvent. Moreover, as with the previously described method, the reduction can be carried out at a temperature ranging from about −30° C. to about 25° C. In a presently preferred embodiment, the reduction is carried out at a temperature ranging from about −5° C. to about 5° C.

In yet another embodiment, the present invention provides a method for isolating an R,S-halomethyl alcohol (R,S-HMA) from a mixture of R,S-HMA and S,S-HMA. S,S-HMA is crystalline and is relatively easy to purify. In contrast, the R,S-HMA is soluble in most organic solvents and is difficult to purify by standard purification techniques, such as recrystallization. Mixtures of R,S-HMA and S,S-HMA can be separated by column chromatography or by preparative scale HPLC, but are not practical economically.

It has now been discovered that a mixture of R,S-HMA and S,S-HMA can be separated on the basis of differential solubility; R,S-HMA is soluble in hot hexanes, whereas the crystalline diastereomer, S,S-HMA, is not. As such, the present invention provides a method for isolating an R,S-halomethyl alcohol (R,S-HMA) from a mixture of R,S-HMA and S,S-HMA, the method comprising: combining the mixture of R,S- and S,S-HMAs with hexane and heating to a temperature ranging from 50° C. to about 60° C. to produce a hexane extractant; cooling the hexane extractant to a temperature ranging from about 0° C. to about 10° C., filtering the hexane extractant to form a first retentate and recovering the first retentate; combining the first retentate with hexane to form a hexane solution, heating the hexane solution to a temperature ranging from about 50° C. to about 60° C., and cooling the hexane solution to a temperature ranging from about 30° C. to about 40° C. to produce a suspension; and filtering the suspension to form a second retentate and recovering the second retentate, wherein the R,S-HMA is present in the second retentate.

For instance, a crude reaction mixture, consisting of 50–90% R,S-HMA, 10–50% S,S-HMA and 0–10% Me-ester, was extracted with hot hexane and the resulting hexane extractant was cooled to 10° C. and filtered to provide about 94% pure R,S-HMA in 74% yield (based on HMK); the major contaminant was S,S-HMA (5%). Attempts to purify the 94% pure material by differential solubility (above treatment) or by recrystallization from a variety of solvent/solvent mixtures were not completely successful. However, it has been determined that the best way to purify the 94% pure R,S-HMA is to dissolve it in hot hexane (about 60° C.), cool to about 40° C., and then allowing the mixture to crystallize at about 35° C. to about 37° C. for at least 2 h. The crystallized product is then filtered at about 30° C. to about 35° C. to provide about 99.5% pure R,S-HMA in 83% recovery. Interestingly, it has been found that if the mixture is cooled to 25° C. and filtered, a mixture consisting of about 94.5% R,S-HMA and 5.5% S,S-HMA, is obtained. This result is surprising because S,S-HMA is more crystalline and is not soluble in hexane, thus suggesting that S,S-HMA, not R,S-HMA, should be the first to crystallize. Although a variety of solvent/solvent mixtures, such as methanol, methanol/water, toluene, dibutyl ether, etc., have been used to purify 94% pure R,S-HMA, the highest degree of purity/recovery is obtained with the hot hexane method of the present invention.

Once prepared and purified, the R,S-HMA can be converted into an R,S-epoxide. As such, in another embodiment, the present invention provides an A method for preparing an R,S-epoxide compound having the following general formula:

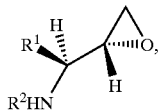

the method comprising: reducing a haloketone (HMK) compound having the following general formula:

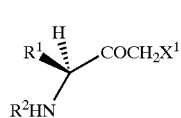

(I)

with a non-coordinating reducing agent to form an R,S-haloalcohol (R,S-HMA) compound having the following general formula:

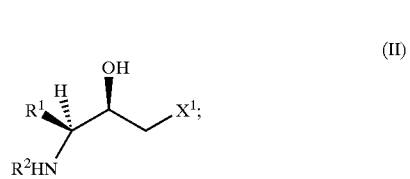

and contacting the R,S-HMA compound of Formula II with an alkali metal base to form the R,S-epoxide compound. It will be readily apparent to those of skill in the art that the foregoing discussions relating to $R^1$, $R^2$ and $X^1$ and their preferred embodiments are fully applicable to this method and, thus, will not be repeated. In a presently preferred embodiment, the non-coordination reducing agent is LATBH and the reduction is carried out in diethyl ether. In another presently preferred embodiment, the alkali metal base is selected from the group consisting of NaOH, KOH, LiOH, $NaOCH_3$, $NaOCH_2CH_3$ and KOtBu. In a further preferred embodiment, KOH is the alkali metal base used. In another embodiment, calcium hydroxide can be used.

In one embodiment of the inversion method, R,S-epoxide is prepared by a four step process illustrated below. More particularly, in one embodiment of the inversion method, the present invention provides a method for preparing an R,S-epoxide having the following general formula:

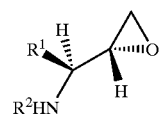

the method comprising: (a) reducing a haloketone (HMK) compound having the following general formula:

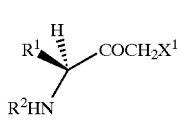

(I)

with a reducing agent to form an S,S-haloalcohol (S,S-HMA) compound having the following general formula:

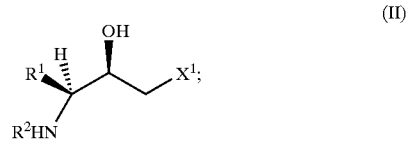

(b) contacting the S,S-HMA compound of Formula II with a member selected from the group consisting of arylsulfonyl halides and alkylsulfonyl halides in the presence of an amine to form an S,S-halomethyl sulfonyl (S,S-HMS) compound having the following general formula:

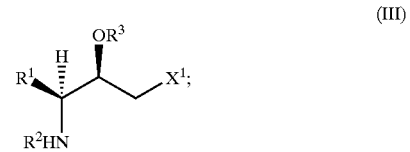

(c) contacting the S,S-HMS compound of Formula III with an acetate in the presence of a phase transfer catalyst and water to form an R,S-halomethyl acetate (R,S-HMAc) compound having the following general formula:

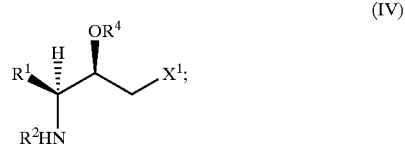

(IV)

and (d) contacting the R,S-HMAc compound of Formula IV with an alkali metal base to form the R,S-epoxide. It will be readily apparent to those of skill in the art that the foregoing discussions relating to $R^1$, $R^2$ and $X^1$ and their preferred embodiments are fully applicable to this method and, thus, will not be repeated. In the above formulae, $R^3$ is a functional group including, but not limited to, arylsulfonyls and alkylsulfonyls. In a presently preferred embodiment, $R^3$ is a member selected from the group consisting of a methylsulfonyl group (i.e., a mesyl group), a toluenesulfonyl group (i.e., a tosyl group), a trifluoromethanesulfonyl group (i.e., a triflate group) and a para-nitrobenzene sulfonyl group (i.e., a nosyl group). It will be readily apparent to those of skill in the art that other leaving groups can be used as $R^3$ in place of the arylsulfonyl and alkylsulfonyl groups. $R^4$, in the above formulae, is an acyl group derived from the acetate. In a presently preferred embodiment, $R^4$ is an acetyl group.

In the first step, i.e., step (a), a HMK is reduced with a reducing agent to form an S,S-HMA. In a preferred embodiment, the reducing agent is selected from the group consisting of sodium borohydride, lithium aluminum hydride and sodium cyanoborohydride. In another preferred embodiment, step (a) is carried out in a solvent. Suitable solvents include, but are not limited to, ethanol, methanol, isopropanol, THF, diethyl ether, etc. The reduction can be carried out at a temperature ranging from about −30° C. to about room temperature and, more preferably, at about −20° C. In a presently preferred embodiment, the reduction step is carried out using sodium borohydride in ethanol to provide a 6:1 mixture of S,S-HMA:R,S-HMA in 98% yield. The S,S-isomer is highly crystalline and can be easily purified by recrystallization to provide >99.8% pure S,S-HMA in 80% yield.

In addition to the foregoing, HMA can also be prepared by Merwin Pondroff Verley reduction of HMK. In this process, HMK is reacted with aluminum isopropoxide in refluxing IPA to give S,S-CMA in high diastereoselectivity. Presumably, under these conditions, the reduction occurs under chelation control and a mixture of S,S-HMA:R,S-HMA with ratios as high as 20:1 is obtained (see, U.S. Pat. Nos. 5,684,176 and 5,847,144, both of which issued to Hilpert).

In the second step, i.e., step (b), an S,S-HMA is reacted with an arylsulfonyl halide or an alkylsulfonyl halide in the presence of an amine to form an S,S-halomethyl sulfonyl (S,S-HMS). Suitable amines include, but are not limited to, trialkylamines (e.g., trimethylamine, triethylamine, etc.), pyridine, 4-dimethylamino pyridine, etc. In a presently preferred embodiment, the amine is triethylamine. Step (b) can be carried out in a variety of different solvents. Exemplar solvents include, but are not limited to, the following: chlorinated solvents (e.g., methylene chloride, dichloroethane, chlorotoluene, etc.), aromatic hydrocarbons (e.g., toluene, xylenes, etc.), ethyl acetate, ethers (e.g., THF, diethyl ether, etc.), etc. In another presently preferred embodiment, step (b) is carried out at a temperature ranging from about −30° C. to about 100° C. and, more preferably, from about 10° C. to about 70° C.

In a particularly preferred embodiment of step (b), the S,S-HMA is reacted with methanesulfonyl chloride in toluene in the presence of an equivalent amount of triethylamine to give the corresponding 2S,3S-CMA Mesylate in 98% yield. The reaction is exothermic and is best conducted at a temperature ranging from about from about 10° C. to about 70° C. The crude mesylate is recrystallized from toluene to provide greater than 95% pure S,S-CMA Mesylate in near quantitative yield. However, in the preferred process, S,S-CMA Mesylate is not isolated and the solution of crude S,S-CMA mesylate in toluene is used, without purification, in the next step, i.e., step (c). Although this mesylation step can be conducted in a variety of solvents, toluene is the preferred solvent because it can be used in the next step, thereby eliminating a solvent exchange step from the process.

In the third step, i.e., step (c), the S,S-HMS is reacted with an acetate in the presence of a phase transfer catalyst and water to from a HMAc. Suitable acetates for use in the present method include, but are not limited to, the following: cesium acetate, potassium acetate, tetrabutylammonium acetate and sodium acetate. In a presently preferred embodiment, the acetate is cesium acetate. A variety of phase transfer catalysts (PTCs) can be used in carrying out step (c). Exemplar phase transfer catalysts include, but are not limited to, crown ethers (e.g., 18-crown-6, dibenzo crown ether, etc.), quaternary ammonium salts and quaternary phosphonium salts (e.g., TATB, aliq. 336, etc.). In a presently preferred embodiment, the phase transfer catalyst is a crown ether. The crown ether 18-crown-6 is particularly preferred because it allows for the production of R,S-HMAc with least amount of side product. Moreover, the rate of reaction with 18-crown-6 is much faster than with any of the other phase transfer catalysts. In addition, 18-crown-6 can be easily removed from the product by a simple water wash.

Step (c), i.e., the displacement reaction, can be carried out in a variety of different solvents. Suitable solvents include, but are not limited to, hydrocarbons (e.g., hexane, heptane, etc.), aromatic hydrocarbons (e.g., toluene, xylene, benzene, etc.) and chlorinated solvents (e.g., $CCl_4$, dichloroethane, chlorotoluenes, etc.). In a presently preferred embodiment, toluene is used as the solvent because it can be used for both steps (b) and (c), and it can be used as a crystallization solvent for the R,S-HMAc. In addition, toluene is commercially available from a variety of sources and can be recycled in high efficiency. The displacement reaction, i.e., step (c) can be carried out at a temperature ranging from about 20° C. to about 100° C. In a presently preferred embodiment, the displacement reaction is carried out at a temperature ranging from about 20° C. to about 100° C.

In addition to the foregoing, it has been found that the displacement reaction is dependent on the amount of water present in the reaction mixture. Presumably, a small amount of water is needed to overcome the lattice energy of the metal acetate, thereby making the nucleophile accessible for the displacement reaction. However, it has been found that increased amounts of water will reduce the reactivity of the nucleophile by solvating it. Thus, in a preferred embodiment, the water is maintained between about 0.5% and about 10.0% and, more preferably, between about 0.5% and about 5%. Once the displacement reaction is completed, the crude product can be isolated by crystallization from, for example, toluene/heptane to give typically greater than 99.5% pure R,S-HMAc in high yield. Alternately, the R,S-HMAc can be isolated and then recrystallized from, for example, methanol/water to give pure R,S-HMAc.

In the final step of the above method, i.e., step (d), the R,S-HMAc is reacted with an alkali metal base to form the R,S-epoxide. It has been found that hydrolysis of the R,S-HMAc followed by subsequent intramolecular ring closure provides the R,S-epoxide in near quantitative yield. In a presently preferred embodiment, the alkali metal base is selected from the group consisting of NaOH, KOH, LiOH, NaOCH$_3$, NaOCH$_2$CH$_3$ and KOtBu. In another preferred embodiment, step (d) is carried out is a solvent. Suitable solvents include, but are not limited to, hydrocarbons, aromatic hydrocarbons, chlorinated solvents and ethers (e.g., THF). In a presently preferred embodiment, the solvent is a mixture of toluene and THF.

In a particularly preferred embodiment of step (d), the R,S-HMAc is reacted with aqueous potassium hydroxide (KOH) in a mixture of THF and ethanol. Evaporation of solvent followed by tituration of the crude product with hexane afforded the desired R,S-epoxide as a low melting, white solid.

Since the R,S-epoxide is soluble in most solvents, it is difficult to purify. In addition, the R,S-epoxide is reactive towards ring opening reactions and will react with potassium hydroxide in ethanol to give the corresponding glycol or the ethoxyglcyol side products. Using this method of the present invention, high purity R,S-epoxide (>>99.5%) has been prepared by incorporating the purity at the R,S-HMAc stage and then maintaining the purity by minimizing side reactions in the final step. Thus, it is important that the above conversion is achieved in near quantitative yield and without formation of side products. Again, in a preferred embodiment of this method, this is accomplished by employing aqueous KOH. Presumably, in this form, the hydroxide is nucleophilic enough to allow hydrolysis to occur, but is not nucleophilic enough to react with the R,S-epoxide and form side products.

Using this method of the present invention, greater than 99.5% pure R,S-epoxide can be prepared in 95–97% yields. The R,S-epoxide prepared by this process can be characterized by NMR, HPLC, TLC and DSC. Moreover, despite difficulties encountered in the prior art relating to the purification of the R,S-epoxide, it has now been discovered that the R,S-epoxide can be purified by recrystallization from petroleum ether. This is an important discovery because traditional purification techniques, such as chromatography, are not applicable due to instability of the R,S-epoxide towards silica gel and alumina. As such, in a preferred embodiment, the above method further comprises: purifying the R,S-epoxide by recrystallization with petroleum ether. An exemplar embodiment of the above method is illustrated by the following reaction scheme:

Preparation of the R,S-Epoxide Using One Embodiment of the Inversion Method

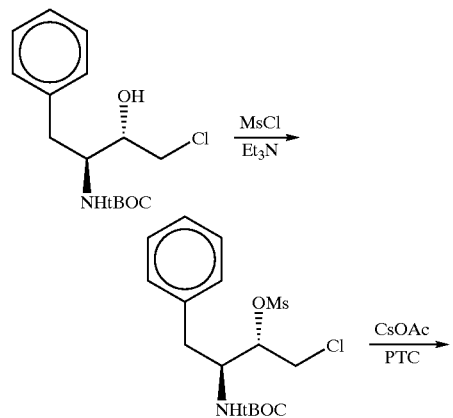

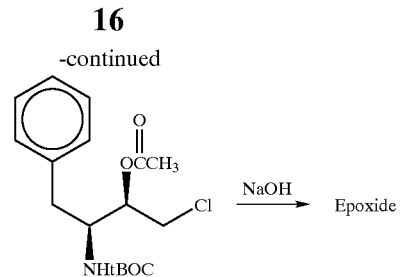

In another embodiment of the inversion method, the present invention provides a method for preparing an R,S-epoxide compound having the following general formula:

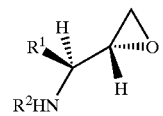

the method comprising: (a) contacting an S,S-halomethyl sulfonyl (S,S-HMS) compound having the following general formula:

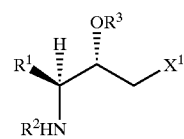

with a carbamate forming acetate to form a cyclic carbamate having the following general formula:

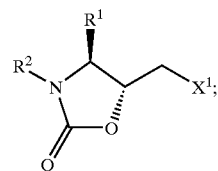

and (b) contacting the cyclic carbamate with an alkali metal base to form the R,S-epoxide. It will be readily apparent to those of skill in the art that the foregoing discussions relating to R$^1$, R$^2$, R$^3$ and X$^1$ and their preferred embodiments are fully applicable to this method and, thus, will not be repeated. A "carbamate-forming acetate," as used herein, refers to an acetate that contains a sufficient leaving group. Exemplar carbamate-forming acetates include, but are not limited to, sodium trichloroacetate, potassium trichloroacetate, tetrabutylammonium trichloroacetate, sodium tribromoacetate, potassium tribromoacetate sodium trifluoroacetate and potassium trifluoroacetate.

As with the previously described methods, step (a) can be carried out in a variety of solvents, such as hydrocarbons (e.g., hexane, heptane, etc.), aromatic hydrocarbons (e.g., toluene, xylene, benzene, etc.) and chlorinated solvents (e.g., CCl$_4$, dichloroethane, chlorotoluenes, etc.). In a preferred embodiment, the solvent is toluene. In step (b) of the above method, the cyclic carbamate is reacted with an alkali metal base to form the R,S-epoxide. In a presently preferred embodiment, the alkali metal base is selected from the group consisting of NaOH, KOH, LiOH, NaOCH$_3$, NaOCH$_2$CH$_3$ and KOtBu. In another preferred embodiment, step (b) is carried out in a solvent. Suitable solvents include, but are not limited to, hydrocarbons, aromatic hydrocarbons, chlorinated solvents and ethers (e.g., THF). In a presently preferred embodiment, the solvent is a mixture of THF and ethanol.

In connection with the above method, the present invention provides a cyclic carbamate compound having the following general formula:

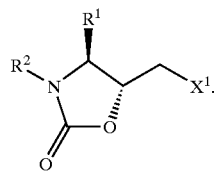

In the above formula, R¹ is an amino acid side chain (e.g., benzyl); R² is hydrogen or a blocking/protecting group (e.g., BOC, MOC, CBZ, etc.); and X¹ is a leaving group (e.g., a chloro or bromo group). This compound can be readily synthesized and purified using the methods set forth in Example II.

C. The Alkene Method

In another embodiment, the present invention provides a method for preparing an alkene having the following general formula:

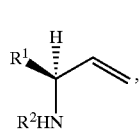
(IV)' the method comprising: (a) contacting a compound having the following general formula:

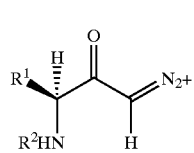
(I)

with a hydrohalo acid to form a compound having the following general formula:

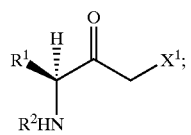
(II)

(b) reducing a compound of Formula II with a reducing agent to form a compound having the following general formula:

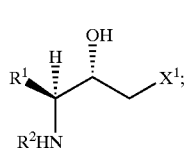
(III)

and (c) dehalohydroxylating a compound of Formula III to form the alkene. It will be readily apparent to those of skill in the art that the foregoing discussions relating to R¹, R² and X¹ and their preferred embodiments are fully applicable to this method and, thus, will not be repeated.

In step (a), a compound of Formula I is reacted with a hydrohalo acid to form a compound of Formula II. Suitable hydrohalo acids include, but are not limited to, hydrobromic acid, hydrochloric acid and hydroiodic acid. In a presently preferred embodiment, the hydrohalo acid is hydrobromic acid or hydrochloric acid. Step (b) can be carried out using any of a variety of reducing agents. In a presently preferred embodiment, sodium borohydride is the reducing agent employed in step (b). Finally, in step (c), compound III is dehalohydroxylated to form the desired alkene. Suitable dehalohydroxylating compounds include, but are not limited to, zinc (0) metals (e.g., zinc dust), nickel metals, zinc mercury amalgan, etc. Step (c) can be carried out in a number of different solvents. Suitable solvents include, but are not limited to, methanol, ethanol, isopropanol, THE, MTBE, toluene, etc. In a presently preferred embodiment, zinc dust in ethanol is used in step (c).

Once prepared, the alkene can be converted to the R,S-epoxide using, for example, m-chloroperbenzoic acid as illustrated below.

In one particularly preferred embodiment of this method, reaction of the diazoketone (i.e. the compound of Formula I), which is prepared from phenylalanine using diazomethane, with hydrobromic acid gives the bromoketone (i.e., the compound of Formula II) in 77% yield. Reduction of the bromoketone with sodium borohydride under conditions similar to those used for the chloroketone gave high selectivity for the S,S-bromomethylalcohol (i.e., the compound of Formula III) over the R,S-diastereomer. The desired S,S-isomer was isolated in 85% yield after recrystallization (see, Parkes, et al., *J. Org. Chem.* 1994 39, 3656).

The bromomethylalcohol was dehalohydroxylated to give the olefin (i.e., the compound of Formula V) by zinc metal in ethanol. Upon work up, the t-BOC protected S-3-amino-4-phenyl-1-butene was isolated in 77% yield. Using this method of the present invention, very pure material was prepared without the problems of racemization associated with the reaction of the t-BOC protected S-phenylalanal route. the alkene was converted to the R,S-epoxide using, for example, a published route using m-chloroperbenzoic acid. An exemplar embodiment of the above method is illustrated by the following reaction scheme:

Preparation of the RS-Expoxide Using the Alkene Method

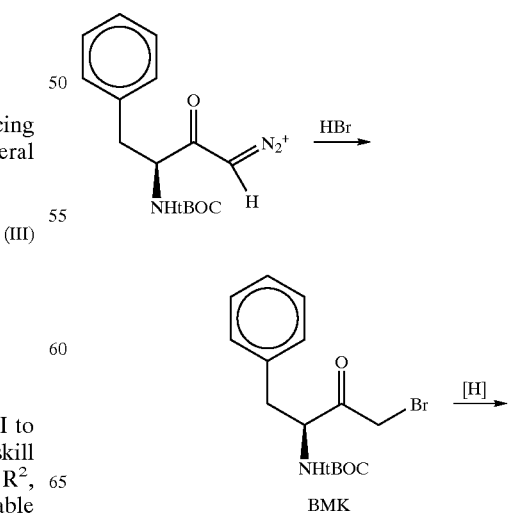

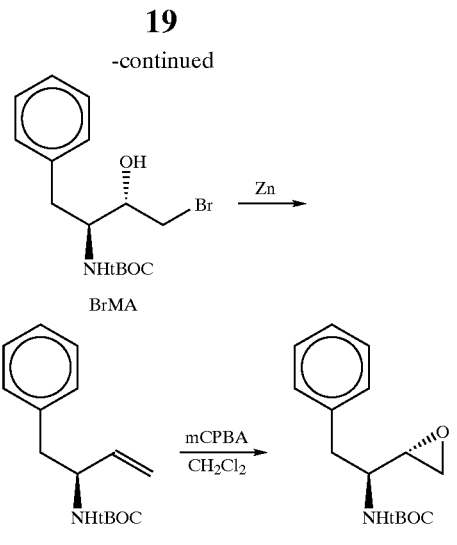

The invention will be described in greater detail by way of specific examples. The following examples are offered for illustrative purposes, and are not intended to limit the invention in any manner. Those of skill in the art will readily recognize a variety of noncritical parameters that can be changed or modified to yield essentially the same results.

EXAMPLES

A. Example I

This example illustrates the preparation of S,S-CMA and R,S-CMA using the reduction methods of the present invention.

1. Preparation of S,S-CMA by Reduction

A 500 mL, 3-necked round bottom flask was fitted with a condenser, thermocouple temperature probe, dry nitrogen inlet, and magnetic stirring. A stirred solution of chloromethylketone (CMK) (19.22 g, 0.0645 mol) and Isopropanol (200 mL) was heated to 50° C. and aluminum isopropoxide (6.87 g, 0.0337 mol, 1.5 eq) was charged to the reactor. The reaction mixture was heated at 50° C. for three hours at which point HPLC analysis indicated 0.4% CMK remained. After heating for 1 additional hour and cooling to room temperature, the reaction was quenched with water (200 mL) and glacial acetic acid (~50 mL) to adjust the pH to 4. The reaction was transferred to a separatory funnel and the organic solids were extracted into ethyl acetate, resulting in two clear phases. The phases were split and the organic phase was evaporated to 18.63 g (97% yield) off-white solid. S,S-Chloromethylalcohol (S,S-CMA): $^1$H NMR (CDCl$_3$): δ 1.37 (s, 9H), 2.97 (m, 2H, J=5.1 Hz), 3.20 (br d, 1H), 3.55–3.69 (m, 2H), 3.83–3.93 (m, 2H), 4.59 (br d, 1H, J=6.6 Hz), 7.21–7.34 (m, 5H); HPLC (Short) $t_R$ 3.84 min=99.51%, 4.66 min=0.49%; HPLC (long) $t_R$ 13.26 min=99.50%, 17.42 min=0.50%.

Proton NMR analysis of final product indicated ~37:1 ratio of S,S:R,S Boc-phenylalanine Chloromethylalcohol (CMA), and traces of acetic acid. HPLC analysis indicated ~32:1 ratio of S,S:R,S CMA (95.1% S,S CMA, 3.0% R,S CMA, 0.6% CMK, and 1.3% impurities from the starting material e.g. methyl ester, boc-phenylalanine). Further purification was accomplished by recrystallization from heptane.

2. Sodium Cyanoborohydride Reduction of CMK

To a solution of sodium cyanaoborohydride (5.28 g, 84.0 mmol, 1.0 eq) in THF (25 mL) was added a solution of CMK (25.0 g, 84.0 mmol) in THF (100 mL), followed by addition of AcOH (10 mL) over 0.5 h at RT. During this addition, internal temperature was never allowed to rise above 42° C. After 1.5 h, TLC analysis of an aliquot indicated total consumption of CMK signaling reaction completion. The reaction mixture was quenched with H$_2$O (250 mL) and the resulting white slurry was stirred at ambient temperature for 1 h. The mixture was extracted with ethyl acetate (500 mL) and then concentrated on a rotary evaporator to a volume of ca. 300 mL. Water (100 mL) and the remaining ethyl acetate was removed under reduced pressure at 45° C. The precipitated product was filtered, washed with water (200 mL), and dried in a vacuum oven at 45° C./28 inch-Hg for 15 h to give 23.8 g (95% yield) of a white solid. HPLC analysis revealed that the solid contained a mixture of 41% R,S-CMA and 59% S,S-CMA.

3. Preparation of R,S-CMA by Reduction with Cerium Chloride/Sodium Borohydride.

A 5000 mL, 3-necked round bottom flask was fitted with mechanical stirring, Claisen head adapter, condenser, dry nitrogen inlet, glass enclosed thermocouple temperature probe, and solids addition funnel, all oven dried at 120° C. and cooled under dry nitrogen. To a stirred slurry of CMK (200 g, 0.672 mol, 1.0 eq), cerium chloride heptahydrate (250 g, 0.672 mol, 1.0 eq), and THF (716 g) was added sodium borohydride (25.5 g, 0.673 mol, 1.0 eq) portionwise over 70 minutes during which time a 4.5° C. exotherm was observed. The reaction mixture was stirred for an additional 5 hours at room temperature, at which time HPLC analysis indicated that starting material had been consumed. The reaction was cooled to 2° C. and ethyl acetate (500 mL) was added. The reaction was quenched with water (1000 mL) at a rate to control the production of hydrogen gas and maintain at a temperature of less than 20° C. The pH of the reaction was adjusted to approximately 6 with glacial acetic acid (18 mL) and additional ethyl acetate (2500 mL) was added to dissolve the solids. The reaction was warmed to room temperature and transferred to a 6000 mL separatory funnel. The organic phase was separated, washed with water and evaporated in vacuo to give 175 g (96% yield) of a white solid. HPLC analysis of the solid indicated 36% R,S boc-phenylalanine chloromethylalcohol (CMA) and 60% S,S CMA; $^1$H NMR analysis confirmed a 0.6:1 R,S:S,S CMA ratio.

4. Preparation of R,S-CMA by Reduction with LATBH.

Lithium tri-t-butoxyaluminohydride (LATBH) (93.87 g, 0.369 mol, 1.1 eq) and anhydrous diethyl ether (500 mL) were placed in a reactor and cooled to 2° C. A solution of CMK (99.84 g, 0.355 mol) and anhydrous diethyl ether (2000 mL) was added over 90 min maintaining an internal temperature of less than 5° C. After the addition was complete, the mixture was stirred for 30 min at which point HPLC analysis indicated no starting material remaining. The reaction was slowly quenched water (1500 mL) and then acetified with glacial acetic acid (1000 mL) at a rate such the temperature was below 10° C. The reaction was warmed to ambient and the organic phase was separated, washed with water and was evaporated in vacuo to give an orange oil (100.12 g). Hexanes (500 mL) was added to the flask and evaporated on the rotary evaporator to remove residual t-butanol and isobutanol; the evaporation yielded an orange oil/solid (97.34 g, 97% yield).

HPLC and $^1$H NMR analysis indicated an approximately 6.5:1 ratio of R,S:S,S CMA. The R,S-isomers was purified by extraction into refluxing hexanes (300 mL), filtration while hot to remove the less soluble S,S-isomer, and slow cooling overnight. After filtration and drying, 74.5 g (82.3% yield) of a product that was 92.1% R,S CMA and 5.4% S,S CMA by HPLC and $^1$H NMR analysis.

5. Purification of Mixtures of S,S- and R,S-CMA

CMA (170 g of a mixture of 0.6 to 1 isomers) and hexanes (800 g) were charged to the flask and heated to reflux for 1 hour. The less soluble isomer mix (90% S,S CMA, 9% R,S CMA) (99.6 g, 58% yield) was removed by filtration of the hot mixture. The filtrate was evaporated to 75% volume, cooled and filtered to give the more soluble isomer mix (94% R,S CMA, 3% S,S CMA) 36.7 g (22% yield) were removed by cold filtration through a 600 mL coarse, sintered glass funnel. The residual filtrate was dryed in vacuo to give a yellow oil (18.6 g, 11% yield) containing a mixture of isomers.

A mixture of 32 g of the crude solid (93% R,S-CMA and 6% S,S-CMA) from the hot hexane recrystallization and hexanes (600 mL) was heated to 60° C. The resulting solution was slowly allowed to cool to 53° C. and seeded with R,S-CMA crystals. Further crystallization was observed at 37° C. at which point significant amount of white needles had formed in solution. The internal temperature was maintained between 35–40° C. for 1.5 h, at which point the mixture was hot filtered to provide 25.7 g (80% recovery) of R,S-CMA as white needles. HPLC analyses revealed that R,S-CMA was 99.8% pure and contained ca. 0.2% S,S-CMA. Concentration of hexane filtrate on a rotary evaporator afforded 6.1 g of a white solid which based on HPLC analysis was found to be consist of 91.9% R,S-CMA and 6.4% S,S-CMA.

R,S-Chloromethylalcohol (R,S-CMA): $^1$H NMR (CDCl$_3$): δ 1.36 (s, 9H), 2.94 (m, 2H, J=7.3 Hz), 3.54 (d, 2H, J=4.6 Hz), 3.77 (m, 1H, J=2.1 Hz), 3.94 (m, 1H, J=7.3 Hz), 4.99 (d, 1H, J=8.8 Hz), 7.24 (br m, 5H); HPLC (Short) t$_R$ 3.87 min=0.21%, 4.69 min=99.79%.

B. Example II

This example illustrates the preparation of R,S,-Epoxide using two different inversion methods. In NMR: Varian 300 MHz; HPLC: Hewlett Packard 1100, column C18 reverse phase using acetonitrile/water with phosphate buffer; melting points were measured by DSC.

1. Preparation of R,S-Epoxide by the Inversion Route Via an Acetate a. Step 1: Mesylation

A 3 L jacketed reactor equipped with a mechanical stirrer, addition funnel, reflux condenser, temperature probe, and a nitrogen gas inlet was charged with S,S-CMA (150.3 g, 0.501 mol) and toluene (1.5 L). The system was flushed with nitrogen and triethylamine (62 g, 0.613 mol) was added. The resulting mixture was treated, dropwise, with methanesulfonyl chloride (69 g, 0.595 mol). The rate of addition of methanesulfonyl chloride was maintained so as to control the reaction temperature below 50° C. When the addition was complete, the reaction mixture was stirred for 1 h, sampled and analyzed by HPLC which indicated that the reaction was complete. The reaction mixture was slowly quenched into 10% aqueous potassium bicarbonate solution, and the organic phase was separated and washed with water. The organic layer containing the mesylate derivative was then dried azeotropically and used without isolation in the displacement reaction. In order to obtain yield/purity data, a sample of reaction mixture was withdrawn and stripped off solvent under reduced pressure to give S,S-CMA mesylate, a pale yellow solid: mp 117–121° C.; $^1$H NMR (CDCl$_3$): δ 1.35 (s, 9H), 2.79 (br t, 1H, J=11.1 Hz), 3.04 (dd, 1H, J=14.4, 4.8 Hz), 3.17 (s, 3H), 3.73 (m, 2H, J=4.5 Hz), 4.15 (ddd, 1H, J=5.1, 4.8, 3.6 Hz), 4.69 (br d, 1H, J=6.6 Hz), 5.04 (br s, 1H), 7.20–7.34 (m, 5H); HPLC revealed that the product was 99.7% (area %) pure.

b. Step 2: Displacement

A second reactor was charged with cesium acetate (241.7 g, 1.125 mol) and 18-crown-6 (33 g, 0.125 mol) in toluene (400 mL) and the mixture was heated to 70C. Next, a solution of S,S-CMA mesylate in toluene was added over 1 h and the resulting mixture was heated at 70° C. for an additional 9 hrs at which time TLC analysis indicated the reaction was complete. The reactor was cooled to 35° C., and water (1 L) was added. The organic layer was separated and washed with water and the solvent was evaporated until the concentration of the product was 20% by weight as determined by 1 H NMR analysis. Heptane (1350 g) was added and the mixture heated to 55° C. for 30 min, and cooled to ambient over 1 h. The mixture was then cooled to 5° C., filtered, and the white solid was dried in vacuo to give 131.5 g (77% yield) of (2R,3S)-N-t-butoxycarbonyl-1-chloro-2-acetoxy-4-phenylbutanamine, a white solid: mp 105–106° C.; $^1$H NMR (CDCl$_3$): δ 1.39 (s, 9H), 2.13 (s, 3H), 2.75 (br d, 2H, J=7.5 Hz), 3.56 (br d, 2H, J=6.3 Hz), 4.24 (ddd, 2H, J=7.4, 2.2 Hz), 4.52 and 4.67 (both br d, 1H total, J=9.6 Hz), 5.03–5.12 (m, 1H, J=6.2, 2.1 Hz), 7.17–7.33 (m, 5H); TLC (silica gel, 30% EtOAc/Hexane): R$_f$=0.75; HPLC analysis revealed that the product was 99.7% pure.

c. Step 3: Hydrolysis and Ring Closure

A 1 L flask fitted with a mechanical stirrer, addition funnel, temperature probe, and a nitrogen inlet was charged with R,S-CMA Acetate (34.3 g, 100.4 mmol), THF (156 mL), ethanol (90 mL) and water (30 mL). The mixture was cooled to 0–3° C. and a 43% aq. KOH solution (13.3 g of 86% potassium hydroxide dissolved in 13.3 mL of water) was added dropwise to the reaction mixture so as to maintain an internal temperature of <5° C. The reaction mixture was stirred at 0–3° C. for 1.5 h and then quenched with 6% aq. sodium biphosphate solution (250 mL); the reaction temperature was maintained below 10° C. during quench. Diethyl ether (260 mL) was added and the organic layer was separated, dried (Na$_2$SO$_4$), filtered, and stripped of solvent under reduced pressure to give a clear oil. Hexane (130 mL) was added and the resulting mixture was concentrated on a rotary evaporator till <10% hexane remained and the residue was seeded with crystals of pure R,S-Epoxide. The mixture was then stored at room temperature for 16 h and the precipitated solid was collected by filtration and dried to provide 25.4 g (96%) of the title compound, a white solid: mp (DSC): 51.56° C.; $^1$H NMR (CDCl$_3$): δ 1.39 (s, 9H), 2.59 (s, 1H), 2.70 (dd, 1H, J=3.9 Hz), 2.91 (m, 2H, J=6.6 Hz), 3.01 (m, 1H, J=3.6 Hz), 4.13 (d, 1H, J=7.8 Hz), 4.49 (d, 1H, J=7.2 Hz), 7.27 (br m, 5H). The purity, as determined by HPLC analysis, was 99.5%.

d. Alternate Process for Preparation of 2R,3S-Chloromethylacetate

A 4 L jacketed reactor equipped with a mechanical stirrer, reflux condenser, temperature probe, and a nitrogen gas inlet was charged with S,S-CMA Mesylate (246.5 g, 0.65 mol) and 18-crown-6 (43.4 g, 0.16 mol), cesium acetate (322.8 g, 1.685.7 mol) and toluene (3.2 L). The resulting mixture was heated at 72° C. for 11 hours, at which point TLC analysis (silica gel, 30% EtOAc/Hexane) indicated the starting material had been consumed. The organic phase was separated and concentrated under reduced pressure to provide a white solid. The residue was dissolved in ethyl acetate (1.2 L) and the resulting solution was washed with H$_2$O (2×550 mL), dried (Na$_2$SO$_4$), filtered, and stripped off solvent under reduced pressure to provide 216 g (97%) of 92% pure R,S-CMA Acetate. Recrystallization of the crude product from 85:15 methanol/water provided 99.7% pure R,S-CMA Acetate in 57% yield. The mother liquor was concentrated on rotary evaporator, treated with water, and chilled to 5° C. to provide an additional 22 g of 98.2% pure product, thus increasing the total yield of R,S-CMA Acetate to 76%.

2. Preparation of R,S-Epoxide by the Inversion Route Via Trichloroacetic Acid a. Step 1: Preparation of 'Cyclic Carbamate'

A 250 mL round-bottom flask equipped with a magnetic stir bar, reflux condenser, temperature probe, and a nitrogen gas inlet was charged with 9.98 g (26.4 mmol) of S,S-CMMs, 0.434 g (1.35 mmol) of tetrabutylammonium bromide (TBAB), 7.46 g (40.2 mmol) of sodium trichloroacetate, and flushed vigorously with $N_2$. Toluene (104 mL, 90 g) was added under a steady stream of $N_2$ and the resulting slurry was heated to ~45° C. The reaction mixture was stirred at 45° C. overnight, at which point TLC analysis (silica gel, 30% EtOAc/Hexane) indicated the starting material had been consumed. The toluene phase was transferred from the reaction vessel into a 500 mL separatory funnel and EtOAc/H2O (50 mL/100 mL), used to rinse the reactor, was combined with the organic layer. After separating the two layers, the organic layer was washed with $H_2O$ (1×100 mL), dried over $Na_2SO_4$, filtered, and removed under vacuum. The resulting crude solid was dried in a vacuum oven (45° C.) overnight to provide a yield of 92% (7.92 g, 24.3 mmol, ~90% pure).

This product was combined with the crude cyclic carbamate (1.67 g, 5.13 mmol) from a previous small scale synthesis (CP078-24) and crystallized from MeOH/$H_2O$ as follows: 9.59 g of crude product was dissolved in 43 mL (34 g) of MeOH while heating to 45° C. To this warm MeOH solution was slowly added 4 mL of $H_2O$ and the temperature allowed to reach ambient without agitation. Needle formation was rapid and the flask was cooled to 0–5° C. prior to filtration, yielding 7.24 g (75.5% recovery) of product (99.42% pure).

b. Step 2: Preparation of R,S-Epoxide

To a 50 mL round-bottom flask equipped with a magnetic stir bar, temperature probe, and a nitrogen inlet was added a 43% aqueous KOH solution (0.73 g soln., 5.82 mmol) and 1.0 g of $H_2O$. The contents of the flask were cooled to 0–3° C. with the aid of an ice-bath. A separate flask was charged with 0.99 g (2.22 mmol) of the 'cyclic carbamate', 3.2 g of THF, and 1.6 g of EtOH and agitated to dissolve all solids. The 'cyclic carbamate' solution was added dropwise to the reaction flask via pipet so as to maintain an internal temperature of <4° C. Once addition was complete, the reaction was stirred at 0–3° C. for ~1 hour, at which point the reaction was quenched by addition of a sodium biphosphate solution (0.448 g $NaH_2PO_4$, 6.8 g $H_2O$). The reaction quench was conducted at such a rate as to keep the internal temperature <10° C. (Note: The reaction was analyzed for completion via TLC after a 30 min. post-stir and found to contain the desired epoxide.) The cloudy reaction mixture was diluted with 10 mL of $Et_2O$ and the layers were separated. The clear organic layer was dried over $Na_2SO_4$, filtered, and the solvent was removed under vacuum to afford a clear oil (0.8 g).

The crude product was taken up in 20% EtOAc/hexanes (due to solubility problems in desired eluent) and purified via column chromatography (silica gel, 10% EtOAc/hexanes). R,S-epoxide, as well as a small amount of a nonpolar impurity, were collected prior to running a gradient to 50% EtOAc/hexanes to collect the deblocked impurity. The two fractions were evaporated of solvent to obtain clear oils: R,S-epoxide: 0.444 g (solidified under vacuum; HPLC: ~90%). The identity of the R,S-epoxide was confirmed by $^1$H NMR, HPLC, and TLC.

c. Mechanistic Discussion

Without intending to be bound by any theory, it is thought that the reaction occurs through the following mechanism. Attack of a trichloroacetate anion on the secondary mesylate in an $SN_2$ fashion inverts the stereochemistry and provides the intermediate R,S-chloromethyltrichloroacetate (R,S-CMAcCl$_3$). Due to the excellent leaving group ability of :CCl$_3$ (trichlorocarbene), nucleophilic attack of the carbamate nitrogen on the acetate carbonyl and subsequent (or concurrent) loss of a proton provides the cyclic carbamate. It is thought that treatment of this species with aqueous base favors reaction of the hydroxide at the cyclic carbonyl, possibly due to the added benefit of relieving the ring strain of the molecule, resulting in the expected epoxide (55–60%).

C. Example III

This example illustrates the preparation of the R,S-epoxide by the epoxidation of an alkene.

1. Preparation of Bromomethyl Ketone (BMK):

A solution of diazomethyl ketone (DMK) in ethyl acetate/diethyl ether (16.8 g solution, 1 g DMK, 3.5 mmol) was cooled to 5° C. and treated dropwise with a solution of hydrobromic acid (1.8 g, 10.6 mmol); the reaction temperature was maintained below 10° C. during the addition. The resulting mixture is stirred at 0–5° C. for 2 hours and quenched with water (20 mL). The organic layer was separated and washed with water (3×20 mL) until the pH of the final water wash was >6. The organic layer was concentrated on a rotary evaporator to give 0.92 g (77%) of an off-white solid. The product purity, as determined by HPLC, was 91%. $^1$H NMR-(S,S-BMK; CDCl$_3$): δ 1.41 (s, 9H), 3.07 (m, 2H, J=6.6 Hz), 3.94 (m, 2H, J=16.2 Hz), 4.72 (q, 1H, J=7.2 Hz), 5.07 (d, 1H, J=7.5 Hz), 7.20–7.31 (br m, 5H).

2. Preparation of Bromomethylalcohol (BMA):

A mixture of bromomethylketone (20.3 g, 59.3 mmol), ethyl acetate (160 mL), and ethanol (240 mL) was cooled to −30° C. and treated, dropwise, with a slurry of sodium borohydride (1.16 g, 30.7 mmol) in ethanol (80 mL). The reaction mixture was stirred at −30° C. for 30 min. and quenched with acetic acid (4 mL); the reaction temperature was maintained below −20° C. during the quench. The reaction mixture was then warmed to room temperature and treated with water (100 mL) and ethyl acetate (150 mL). The layers were separated and the organic layer was filtered to give 2.8 g of 96.6% pure S,S-BMA. The organic layer was then dried (Na$_2$SO$_4$), filtered, and evaporated in vacuo to give 14.2 g of a mixture consisting of 85% S,S-BMA, 6% R,S-BMA, and 5% methyl ester. $^1$H NMR (S,S-BMA; CDCl$_3$): δ 1.36 (s, 9H), 2.98 (br m, 2H, J=4.5 Hz), 3.46 (br m, 1H, J=9 Hz), 3.54 (br m, 1H), 3.86 (br s, 2H), 4.56 (br s, 1H), 7.20–7.31 (m, 5H); HPLC (Short) $t_R$ 2.29 min= 0.07%, 3.88 min=2.68%, 4.29 min=96.61%, 5.25 min= 0.64%.

3. Preparation of BOC-Alkene:

A mixture of crude BMA (12.1 g, 35.2 mmol) prepared above and ethanol (240 mL) was heated to reflux and zinc dust (22.4 g, 343 mmol) was added. The resulting mixture was refluxed for 5 h, at which time TLC analysis (silica gel, 30% EtOAc/Hexane) indicated the starting material had been consumed. The reaction mixture was cooled to room temperature, unreacted zinc dust was removed by filtration, and the filtrate was concentrated in vacuo to give an oil. This oil was dissolved in ethyl acetate (100 mL) and washed with 2% aqueous acetic acid (50 mL). The organic layer was separated, dried (Na$_2$SO$_4$), filtered and evaporated to give 7.5 g of crude product, an oil; this oil solidified on standing at room temperature to give a white solid. The solid was dissolved in methylene chloride (50 mL) and the solution was filtered through 10 g of silica gel. Evaporation of the solvent gave 6.0 g (77% yield of the desired olefin. HPLC analysis showed the olefin was >99% pure. BOC-Alkene: $^1$H NMR (CDCl$_3$): δ 1.40 (s, 9H), 2.83 (br d, 2H, J=6.6 Hz), 4.43 (br s, 2H), 4.56 (br s, 2H), 5.06–5.13 (m, 2H, J=17.4, 10.5, 1.2 Hz), 5.8 (ddd, 2H, J=17.1, 10.5, 5.4 Hz), 7.20–7.31 (m, 5H); IR (thin film): ν 3359 (NH), 1686 (CO), 1645 (alkene); HPLC (Short) t$_R$ 3.87 min=0.65%, 4.01 min=0.04%, 4.69 min=0.19%, 8.38 min=99.12%; MS, m/e MH$^+$ 248.1661.

4. R,S-Epoxide by Alkene Route:

A mixture of BOC-alkene (0.498 g, 2.02 mmol), meta-chloroperbenzoic acid (1.93 g, 8.1 mmol) and dichloromethane (22 mL) was stirred at ambient temperature for 3 h at which time HPLC analysis indicated the starting material had been consumed. The reaction mixture was quenched with aqueous 10% Na$_2$SO$_3$ (60 mL), and diluted with diethyl ether. The organic layer was washed with cold saturated Na$_2$CO$_3$ (60 mL), brine (60 mL), dried over Na$_2$SO$_4$, and the solvent evaporated to provide a clear oil that solidified on standing. A white solid (0.49 g, 1.86 mmol) was isolated in 92% yield and was shown to be a 5.2:1 mixture of R,S- and S,S-epoxide, respectively (HPLC, 96.5% pure combined). Analysis of the product mixture by proton NMR spectroscopy indicated an approximate 5.7:1 ratio of diasteriomeric epoxides and no alkene starting material.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method for preparing an R,S-epoxide compound having the following general formula:

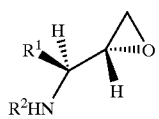

said method comprising:

(a) contacting an S,S-halomethyl sulfonyl (S,S-HMS) compound having the following general formula:

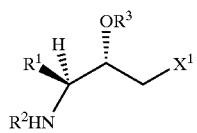

with a carbamate-forming acetate containing a sufficient leaving group to form a cyclic carbamate having the following general formula:

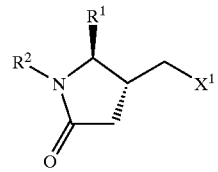

and (b) contacting said cyclic carbamate with an alkali metal base to form said R,S-epoxide;

wherein:

R$^1$ is an amino acid side chain;

R$^2$ is a blocking group;

R$^3$ is a member selected from the group consisting of arylsulfonyls and alkylsulfonyls; and X$^1$ is a leaving group.

2. The method in accordance with claim 1, wherein R$^3$ is a member selected from the group consisting of methylsulfonyl and toluenesulfonyl.

3. The method in accordance with claim 1, wherein said carbamate-forming acetate is a member selected from the group consisting of sodium trichloroacetate, potassium trichloroacetate, tetrabutylammonium trichloroacetate, sodium tribromoacetate, potassium tribromoacetate sodium trifluoroacetate and potassium trifluoroacetate.

4. The method in accordance with claim 1, wherein said carbamate-forming acetate is sodium trichloroacetate.

5. The method in accordance with claim 1, wherein step (a) is carried out in toluene.

6. The method in accordance with claim 1, wherein said alkali metal base is a member selected from the group consisting of NaOH, KOH, LiOH, NaOCH$_3$, NaOCH$_2$CH$_3$ and KOtBu.

7. The method in accordance with claim 1, wherein said sufficient leaving group is selected from the group consisting of trichlormethyl, tribromomethyl and trifluoromethyl.

8. The method in accordance with claim 1, wherein R$^1$ is a member selected from the group consisting of a side chain from any of the naturally occurring amino acids and amino acids mimetics; R$^2$ is a blocking group selected from the group consisting of BOC, MOC and CBZ; and X$^1$ is a leaving group selected from the group consisting of Cl, Br and F.

9. The method in accordance with claim 8, wherein R$^1$ is a side chain from any of the naturally occurring amino acids.

10. The method in accordance with claim 1, wherein R$^1$ is a member selected from the group consisting of a benzyl, a substituted benzyl, an S-phenyl, an alkyl and a para-nitrobenzene.

11. The method in accordance with claim 10, wherein R$^1$ is benzyl.

12. The method in accordance with claim 8, wherein R$^2$ is BOC.

13. The method in accordance with claim 1, wherein X$^1$ is a chloro or bromo group.

14. The method in accordance with claim 1, wherein R$^1$ is benzyl; R$^2$ is BOC; R$^3$ is methylsulfonyl; and X$^1$ is a bromo or chloro group.

* * * * *